United States Patent [19]

Frulla et al.

[11] Patent Number: 4,550,188
[45] Date of Patent: Oct. 29, 1985

[54] PREPARATION OF CARBAMATES

[75] Inventors: Floro F. Frulla, Wallingford; Fred A. Stuber, North Haven; Peter J. Whitman, Hamden, all of Conn.

[73] Assignee: The Dow Chemical Company, Midland, Mich.

[21] Appl. No.: 625,060

[22] Filed: Jun. 27, 1984

[51] Int. Cl.$^4$ ............... C07C 125/065; C07C 125/073
[52] U.S. Cl. ........................................ 560/24; 560/12; 560/25
[58] Field of Search ............................. 560/24, 25, 12

[56] References Cited

U.S. PATENT DOCUMENTS

| | | | |
|---|---|---|---|
| 2,762,845 | 9/1956 | Stroh et al. | 260/578 |
| 3,763,217 | 10/1973 | Brill | 560/24 |
| 4,100,351 | 7/1978 | Romano et al. | 560/24 |
| 4,268,683 | 5/1981 | Gurgiolo | 560/24 |
| 4,268,684 | 5/1981 | Gurgiolo | 560/24 |
| 4,395,565 | 7/1983 | Romano et al. | 560/24 |

FOREIGN PATENT DOCUMENTS 48371  3/1982  European Pat. Off. .

Primary Examiner—Bernard Helfin
Attorney, Agent, or Firm—James S. Rose; Michael S. Jenkins

[57] ABSTRACT

Disclosed is an improved process for the preparation of carbamates by heating an organic carbonate and an aromatic amine in the presence of aluminum as catalyst and a promoter comprising a combination of iodine and a mercury salt.

High reaction temperatures are avoided by the process and conversions to carbamate products are high. Additionally, the process is economically attractive because even the common aluminum foil can be used as the catalyst.

The products prepared by the process can be used in the production of insecticides, and, particularly, as intermediates in the preparation of organic mono- and polyisocyanates.

19 Claims, No Drawings

PREPARATION OF CARBAMATES

BACKGROUND OF THE INVENTION

1. Field of the Invention

This invention relates to carbamates and is more particularly concerned with an improved process for the preparation of carbamates from aromatic amines and organic carbonates.

2. Description of the Prior Art

The preparation of carbamates, particularly aromatic carbamates, has received a considerable degree of attention in the prior art. Originally prepared by the reaction of amines with chloroformates or from the reaction of isocyanates with alcohols, newer preparative methods being investigated include, inter alia, the reaction of organic carbonates with amines.

In respect of the latter method, Brill in U.S. Pat. No. 3,763,217 was one of the first to disclose the preparation of N-substituted carbamates by reacting organic carbonates with amines in the presence of a Lewis acid as a catalyst. Overall yields and conversions are low by this method.

Romano et al in U.S. Pat. No. 4,100,351 disclosed that carbamates are formed in improved selectivity and conversion if dialkyl carbonates are reacted with the N-acyl derivatives of aromatic amines in the presence of Lewis acids and more particularly halides, alcoholates, and phenates of aluminum and titanium.

Gurgiolo in U.S. Pat. No. 4,268,683 discloses the use of certain zinc or divalent tin halides or zinc or divalent tin salts of monovalent organic compounds having a pKa of at least 2.8 as catalysts in the reactions of organic carbonates with aromatic amines. Other related catalysts for this same reaction are reported by Gurgiolo in U.S. Pat. No. 4,268,684 and include, inter alia, zinc, tin, and cobalt salts of monocarboxylic acids having a pKa value of less than 2.8. However, in the case of the former reference, conversions to carbamates are generally low even at reaction temperatures as high as 200° C. and pressure conditions are required to obtain good conversions. The latter reference calls specifically for reaction temperatures of at least 200° C. and pressure conditions. Even then carbamate yields are not consistently high.

Romano et al in U.S. Pat. No. 4,395,565 employ reasonably low temperature conditions and alkali metal or alkaline earth metal catalysts in converting aromatic amines and alkyl carbonates to carbamates but still consistently high conversions are not possible.

European Pat. No. 48,371 does report the formation of carbamates in reasonably high yields when amines and carbonates are reacted in the presence of certain neutral or basic organic and inorganic compounds of lead, titanium, zinc, or zirconium as catalysts.

Surprisingly, it has now been discovered that aluminum metal in combination with traces of a promoter combination will catalyze the reaction of aromatic amines and carbonates to form carbamates in high conversions. What makes this discovery even more surprising is the fact that the prior art (see U.S. Pat. No. 2,762,845) has shown that aluminum, optionally in the presence of mercuric chloride, catalyzes the reaction of aniline with olefins via the formation of an aluminum anilide to yield ortho-alkylated products. That is to say, alkylation with olefins takes place at the ortho carbons and not at the nitrogen. Conversely, in the present method, the reaction takes place at nitrogen rather than at the ortho carbons.

Compared with the prior art methods, the process in accordance with the present invention provides an improvement because low cost aluminum in any form can be used along with only trace amounts of the promoter combination which will be discussed below. Low power requirements are also part of the improvement because reaction temperatures are relatively low and the process need not be conducted under pressure conditions in order to achieve the high conversions to carbamates.

SUMMARY OF THE INVENTION

This invention comprises an improved process for the preparation of carbamates by heating an organic carbonate and an aromatic amine in the presence of a catalyst wherein the improvement comprises employing aluminum as catalyst with a promoter comprising a combination of a mercury salt and iodine.

DETAILED DESCRIPTION OF THE INVENTION

The improved process in accordance with the present invention can be carried out using any of the reactants and reaction procedures and techniques disclosed in the prior art for the preparation of carbamates from aromatic amines and carbonates. The novel feature of the present process, which will be discussed in detail below, resides in the use of aluminum metal as a catalyst along with the promoter combination comprising the mercury salt and iodine. The following equation shows, by way of illustration only, the formation of a methyl carbamate and by-product methanol from the reaction of an aromatic primary or secondary amine with dimethyl carbonate.

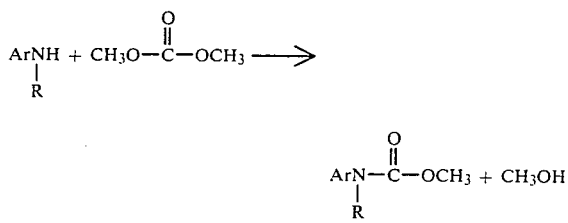

Ar represents an aromatic radical and R can be hydrogen, alkyl, aralkyl, and the like.

The term "aromatic radical" means the radical obtained by removing one nuclear hydrogen atom from an aromatic compound having from 6 to 36 carbon atoms and is inclusive of radicals having the formulae

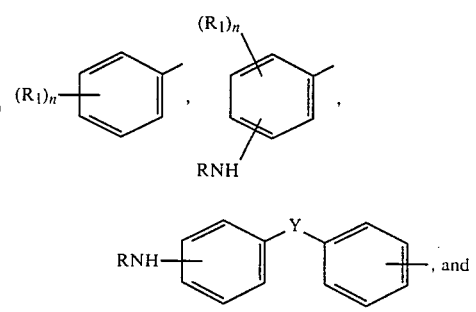

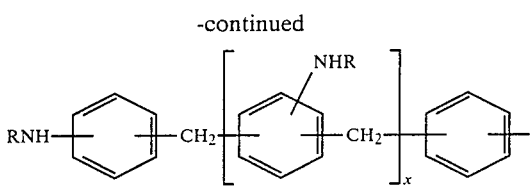

wherein R has the same significance set forth above, $R_1$ is selected from the group consisting of hydrocarbyl and inert substituents, n is 0 to 2, Y is selected from the group consisting of —O—, —CO—, —SO$_2$—, and a single bond, and x is an integer from 0 to 6 or in the case of a mixture x has a mean value greater than 0 but less than 1.

The term "hydrocarbyl" means the monovalent radical obtained by removing one hydrogen atom from the parent hydrocarbon having from 1 to 8 carbon atoms. Illustrative of hydrocarbyl are alkyl such as methyl, ethyl, propyl, butyl, pentyl, hexyl, octyl, and the like, including isomeric forms thereof; alkenyl such as vinyl, allyl, butenyl, pentenyl, hexenyl, octenyl, and the like, including isomeric forms thereof; aralkyl such as benzyl, phenethyl, and the like; aryl such as phenyl, tolyl, xylyl, and the like; cycloalkyl such as cyclobutyl, cyclopentyl, cyclohexyl, cycloheptyl, cyclooctyl and the like including isomeric forms thereof; and cycloalkenyl such as cyclopentenyl, cyclohexenyl, cycloheptenyl, cyclooctenyl, and the like, including isomeric forms thereof.

The term "inert substituent" means any radical other than hydrocarbyl defined above which does not react with the amino groups or otherwise interfere with the process in accordance with the present invention. Illustrative of such substituents are halo, i.e. chloro, bromo, fluoro and iodo; nitro; alkoxy from 1 to 8 carbon atoms, inclusive, such as methoxy, ethoxy, propoxy, butoxy, pentyloxy, hexyloxy, heptyloxy, octyloxy and the like, including isomeric forms thereof; alkylmercapto from 1 to 8 carbon atoms, inclusive, such as methylmercapto, ethylmercapto, propylmercapto, butylmercapto, pentylmercapto, hexylmercapto, heptylmercapto, octylmercapto, and the like, including isomeric forms thereof; and cyano.

The terms "alkyl" and "aralkyl" in respect of the radical R have the same definitions set forth above in the hydrocarbyl group. R is preferably hydrogen.

It is to be understood that when the amine reactant is a polyamine the product would be the corresponding polycarbamate. For detailed descriptions in respect of these procedures and for the aromatic amines and carbonates which can be employed see U.S. Pat. Nos. 4,268,683; 4,268,684 and 4,395,565, whose disclosures are hereby incorporated by reference.

Any of the aromatic primary or secondary amines including mono and polyamines disclosed in the prior art cited supra (and already incorporated herein by reference) can be employed in the present process. However, the aromatic primary amines are preferred including the monoamines and polyamines.

Typical, but not limiting of the aromatic amines which can be used are aniline, p-methoxyaniline, p-chloroaniline, o-, m- or p-toluidine, 2,4-xylidine, 2,4-, and 2,6-toluenediamine and mixtures thereof, m- or p-phenylenediamine, 4,4'-diphenylenediamine, methylenebis(aniline) including 4,4'-methylenebis(aniline), 2,4'-methylenebis(aniline), 4,4'-oxybis(aniline), 4,4'-carbonylbis(aniline), 4,4'-sulfonylbis(aniline), polymethylene polyphenyl polyamines which comprise a mixture of methylene bridged polyphenyl polyamines containing from about 20 to about 90 percent by weight of methylenebis(aniline) and the remainder of the mixture being methylene bridged polyphenyl polyamines having a functionality greater than 2, and the like.

A preferred group of amines consists of aniline, 2,4-, and 2,6-toluenediamine and mixtures thereof, and the methylenebis(anilines) including 4,4'- and 2,4'-methylenebis(aniline) and mixtures thereof.

The carbonates can be any of the organic esters of carbonic acid disclosed in the art cited supra including the dialkyl, diaryl, diaralkyl, and cyclic esters which, illustratively includes dimethyl carbonate, diethyl carbonate, dipropyl carbonate, dibutyl carbonate, diamyl carbonate, dihexyl carbonate, methyl ethyl carbonate, diphenyl carbonate, dibenzyl carbonate, ethylene carbonate, propylene carbonate, and the like.

A preferred group comprises the dialkyl carbonates such as dimethyl carbonate, diethyl carbonate, dipropyl carbonate, and dibutyl carbonate.

The proportions in which the carbonate and the amine are employed are in no way critical to the process in accordance with the invention. Obviously, to obtain complete conversion of amine to carbamate the carbonate must be present in at least a molar equivalency for each equivalent of amine present (molecular weight of aromatic amine divided by the number of amine groups).

Generally speaking, it is preferred that the carbonate be employed in excess over the amine to minimize side reactions (the formation of ureas) and to serve as a solvent for the reaction. Advantageously, the carbonate is employed in at least a 5 molar excess over the aromatic amine, and, preferably, in a range of from about 5 to about 30 moles of carbonate per mole of amine.

The aluminum catalyst can be used as either the pure metal or as an alloy thereof. If an alloy is employed, the aluminum should be the major constituent thereof, i.e. at least 50 percent by weight. Typical of such alloys are aluminum/copper/silicon (87.5%/3.5%/9.0% by weight), aluminum/magnesium (90%/10% by weight), and the like. The pure metal is preferred.

The form in which the aluminum is employed is in no way critical and can be a finely divided powder or as pieces of aluminum rods, sheets, scrap, strips of aluminum foil, and the like.

The optimum quantity of aluminum to be used in any given reaction will vary somewhat depending on the reactants and conditions but can be readily determined by one skilled in the art. Advantageously, the aluminum is employed in an amount of from about 0.1 mole to about 1 mole per mole of aromatic amine, and, preferably, from about 0.2 to about 0.5 mole per mole of amine.

The promoter in accordance with the present process comprises the combination of iodine and a mercury salt. The term "mercury salt" means a mercurous or mercuric salt inclusive of inorganic and organic salts such as mercurous chloride, mercurous fluoride, mercurous bromide, mercurous nitrate, mercurous sulfate, mercurous acetate, mercuric chloride, mercuric iodide, mercuric bromide, mercuric fluoride, mercuric sulfate, mercuric nitrate, mercuric acetate, mercuric basic carbonate, and the like.

The preferred mercury salts are in the mercuric state.

A preferred promoter combination comprises mercuric chloride and iodine.

As is usually the case with catalyzed reactions involving a promoter, the role of the promoter mixture is not well understood. Generally speaking, just trace amounts of the promoters will give rise to the improved process in accordance with the present invention. Advantageously, the iodine and mercuric salt are each employed in an amount falling within the proportions of about 0.001 part by weight to 1 part by weight per mole of aromatic amine, preferably, about 0.01 to 0.5 part by weight per mole of aromatic amine.

One of the particular advantages of the present process is the fact that it is carried out under atmospheric pressure and relatively low reaction temperatures. This is not to say that the process cannot be conducted under pressure conditions if one so chooses. However, there is no particular need to do so as very high conversions to desired carbamates are achieved at normal atmospheric conditions which is, in turn, related to the relatively low temperature conditions employed. In this connection, the reaction is generally conducted at a temperature of from about 75° C. to about 200° C., preferably from about 100° C. to about 150° C., most preferably from about 100° C. to about 130° C.

The reactants along with the catalyst and promoter combination can be mixed in any order and heated to a reaction temperature falling within the above ranges until the reaction is judged to be complete. The completion of the reaction is easily determined using known standard analytical procedures to assay the disappearance of the reactants or maximum appearance of carbamate. Typical methods are infrared absorption analysis, gel permeation chromatography, high pressure liquid chromatography, and the like.

A particularly preferred means for carrying out the process in accordance with the present invention which reduces the tendency for the formation of urea side-products, comprises preheating a mixture of the aromatic amine and carbonate to a temperature of at least about 50° C., preferably between about 50° C. to about 100° C. prior to coming into contact with the catalyst and promoter. Then the aluminum and promoter combination is added to the preheated mixture and thereafter the reaction mixture is heated at a temperature of from about 100° C. to about 150° C., preferably from about 100° C. to about 130° C.

The carbamates are isolated from the reaction mixture using standard separation procedures. Typically, the reaction solution is mixed with water and the carbamate is extracted from the aqueous solution using a water insoluble organic solvent, for example a halogenated solvent such as chloroform, carbon tetrachloride, methylene dichloride, and the like. The organic solution is separated from the aqueous phase and the solvent removed using standard methods to provide the residual carbamate. The carbamate, if desired, can be purified using standard methods such as recrystallization, column chromatography, and the like.

The process in accordance with the present invention is notable for the high conversions of amines to carbamates, the reduction in the formation of the urea by-products, and the accomplishment of these features at relatively low reaction temperatures compared with the prior art. Additionally, the advantages derived from the use of aluminum catalyst and the extremely small quantities of the promoters makes the present process economically attractive.

The carbamate products produced in accordance with the present process are used in a number of applications including the production of pesticides, and, particularly, as intermediates for the preparation of organic isocyanates by thermal cracking of the carbamate into the isocyanate and alcohol.

The following examples describe the manner and process of making and using the invention and set forth the best mode contemplated by the inventors of carrying out the invention but are not to be construed as limiting.

EXAMPLE 1

The following experiment describes the preparation of ethyl-N-phenylcarbamate in accordance with the present invention.

A 250 ml. three-neck reaction flask was equipped with a mechanical stirrer, thermometer, reflux condenser, and a nitrogen inlet tube. The flask was charged with 7.5 g. (0.081 mole) of aniline, 96.2 g. (0.815 mole) of diethyl carbonate, 0.5 g. (0.019 mole) of aluminum foil (Alcoa Wrap TM) cut into small strips, a very small quantity of iodine (estimated about 0.01 g.), and about the same quantity (0.01 g.) of mercuric chloride.

Under a steady nitrogen purge and during stirring the reaction mixture was heated in an oil bath controlled to about 140° C. During the first few hours of heating while the reaction temperature was rising slowly up to about 129° to 130° C., 0.45 liter of evolved hydrogen was measured using a wet test meter. The hydrogen was formed from the reaction of the aniline and aluminum to form aluminum anilide. The total reaction time was about 17.5 hours at about 130° C.

The reaction solution was mixed with 200 ml. of deionized water and the aqueous solution was extracted with 3×50 ml. portions of methylene dichloride. The separated aqueous phase contained a gelatinous precipitate (aluminum hydroxide) which was collected by filtration and the precipitate washed several times with fresh methylene dichloride which was added to the main methylene dichloride solution. The combined organic phases were dried by storage over sodium sulfate and then the solvent stripped using a rotary evaporator under about 15 mm of mercury pressure and a heating bath at about 60° C. The residue was 11.6 g. of an amber colored liquid which solidified upon vacuum drying at 100° C.

A sample of the residue was analyzed by high pressure liquid chromatography (hplc) employing a 3.9 mm×30 cm $\mu C_{18}$ column (Waters) using acetonitrile/water isocratic, 45/55 v/v at a flow rate of 1.5 cc./minute and pressures around 118 atm. By the use of internal standards, the yields of the products obtained from the reaction were determined as follows: aniline=5.2%, ethyl-N-phenylcarbamate=92.4%, diphenyl urea=0.7%, and N-ethylaniline=1.6%.

EXAMPLE 2

The following experiment describes the preparation of 4,4'-methylenebis(N-carbethoxyaniline) in accordance with the present invention.

The same apparatus and procedure set forth in Example 1 was used except that the reaction flask was equipped with a calcium sulfate drying tube to protect against the entrance of any atmospheric moisture into the system and a 4 inch tube adapter packed with 5° Angstrom molecular sieves was placed between the reflux condenser and the reaction flask to ensure moisture free conditions. The flask was charged with 8.0 g. (0.04 mole) of 4,4'-methylenebis(aniline) and 136.2 g.

(1.15 moles) of diethyl carbonate. This mixture was heated using an oil bath set to cycle at 140° C. When the mixture was at 100° C., 0.5 g. (0.019 mole) of aluminum foil (Kaiser Wrap) cut into small pieces was added to the reaction mixture along with about 0.01 g. of iodine and about 0.01 g. of mercuric chloride. The temperature rose slowly up to about 130° C. and was allowed to stay there and reflux for a total reaction period of 16 hours.

The reaction solution was worked up in exactly the same manner as that of Example 1 and provided a residual oil when the methylene dichloride was removed which solidified on standing; weight=12.68 g.

Hplc analysis of a sample of the residue using the column conditions described above in Example 1 and with a solvent system consisting of water/acetonitrile/tetrahydrofuran (isocratic, 48/50/2 v/v/v) showed the following constituents expressed as weight percent of the residue: 0.2 percent 4,4'-methylenebis(aniline), 92.4 percent of 4,4'-methylenebis(N-carbethoxyaniline), and the remaining 7.4 percent consisted of the monocarbamate of the 4,4'-methylenebis(aniline) along with urea oligomers. The above weight percent proportions for the 4,4'-methylenebis(aniline) and 4,4'-methylenebis(N-carbethoxyaniline) are equivalent to a 0.3 percent recovery of starting material and 85.8 percent yield of desired product.

We claim:

1. In a process for the preparation of carbamates by heating at a temperature of from about 75° C. to about 200° C. an organic carbonate selected from the group consisting of dialkyl, diaryl, diaralkyl, and cyclic esters of carbonic acid and an aromatic primary amine in the presence of a catalyst, the improvement which comprises employing aluminum metal as the catalyst with a promoter comprising a combination of a mercury salt and iodine.

2. A process according to claim 1 carried out by (i) preheating a mixture of said organic carbonate and said aromatic amine to a temperature of at least about 50° C.; (ii) adding said aluminum catalyst and said promoter combination to said preheated mixture; and (iii) thereafter heating the reaction mixture at a temperature of from about 100° C. to about 150° C.

3. A process according to claim 1 wherein said aluminum catalyst is employed in an amount of from about 0.1 mole to about 1 mole per mole of aromatic amine.

4. A process according to claim 1 wherein said mercury salt and said iodine are each employed in an amount falling within the proportions of about 0.001 part to 1 part by weight per mole of aromatic amine.

5. A process according to claim 1 wherein said organic carbonate is employed in at least a 5 molar excess in respect of said aromatic amine.

6. A process according to claim 1 wherein said organic carbonate is a dialkyl carbonate.

7. A process according to claim 6 wherein said carbonate is diethyl carbonate.

8. A process according to claim 1 wherein said mercury salt is in the mercuric state.

9. A process according to claim 8 wherein said salt is mercuric chloride.

10. A process according to claim 1 wherein said aromatic amine is aniline.

11. A process according to claim 1 wherein said aromatic amine is polyamine.

12. A process according to claim 11 wherein said amine is methylenebis(aniline).

13. A process for preparing a carbamate from a dialkyl carbonate and an aromatic primary amine said process comprising,
(i) preheating a mixture comprising said dialkyl carbonate and said aromatic amine to a temperature of at least about 50° C.;
(ii) adding to said preheated mixture an aluminum catalyst and a promoter comprising a combination of a mercuric salt and iodine; and
(iii) heating the reaction mixture at a temperature of from about 100° C. to about 150° C.

14. A process according to claim 13 wherein said aluminum catalyst is employed in an amount of from about 0.1 mole to about 1.0 mole per mole of aromatic amine.

15. A process according to claim 13 wherein said mercuric salt and said iodine are each employed in an amount falling within the proportions of about 0.001 part to 1 part by weight per mole of aromatic amine.

16. A process according to claim 13 wherein said mercuric salt is mercuric chloride.

17. A process according to claim 13 wherein said dialkyl carbonate is diethyl carbonate.

18. A process according to claim 13 wherein diethyl carbonate and aniline are converted to ethyl-N-phenyl-carbamate.

19. A process according to claim 13 wherein diethyl carbonate and 4,4'-methylenebis(aniline) are converted to 4,4'-methylenebis(N-carbethoxyaniline).

* * * * *